United States Patent [19]

Kennamer et al.

[11] Patent Number: 5,385,844
[45] Date of Patent: Jan. 31, 1995

[54] POLYMER CONTAINING CONTROL REAGENTS AND POLYMERS USEFUL IN CONTROL REAGENTS

[75] Inventors: Jim Kennamer, Indianapolis, Ind.; Arthur Usmani, University of Kuwait, Kuwait

[73] Assignee: Boehringer Mannheim Corporation, Indianapolis, Ind.

[21] Appl. No.: 51,149

[22] Filed: Apr. 22, 1993

[51] Int. Cl.$^6$ .............................................. G01N 31/00
[52] U.S. Cl. ................................... 436/13; 436/14; 436/16; 436/95; 422/56; 422/57
[58] Field of Search ................ 436/8, 10, 11, 13, 14, 436/15, 16, 17, 95, 111; 422/56, 57

[56] References Cited

U.S. PATENT DOCUMENTS

| | | | |
|---|---|---|---|
| 3,629,142 | 12/1971 | Marbach | 252/408 |
| 3,876,375 | 4/1975 | Maurukas | 23/230 |
| 3,955,925 | 5/1976 | Porksch et al. | 23/230 |
| 3,973,913 | 8/1976 | Louderback | 23/230 |
| 4,121,905 | 10/1978 | Maurukas | 23/230 |
| 4,141,856 | 2/1979 | Dorwart, Jr. | 252/408 |
| 4,183,847 | 1/1980 | Deshmukh | 260/112 |
| 4,189,401 | 2/1980 | Louderback | 252/408 |
| 4,201,694 | 5/1980 | Louderback | 252/408 |
| 4,230,601 | 10/1980 | Hill | 252/408 |
| 4,288,343 | 9/1981 | Louderback | 252/408 |
| 4,289,649 | 9/1981 | Harders et al. | 252/408 |
| 4,298,498 | 11/1981 | Rehner et al. | 252/408 |
| 4,299,726 | 11/1981 | Crews et al. | 252/408 |
| 4,344,864 | 8/1982 | Louderback et al. | 252/408 |
| 4,362,697 | 12/1982 | Tabb et al. | 422/56 |
| 4,403,038 | 9/1983 | Asakura et al. | 436/16 |
| 4,438,202 | 3/1984 | Engler et al. | 436/8 |
| 4,478,944 | 10/1984 | Gross et al. | 436/95 |
| 4,627,014 | 12/1986 | Lo et al. | 436/97 |
| 4,643,976 | 2/1987 | Hoskins | 436/15 |
| 4,649,120 | 3/1987 | Steur et al. | 436/13 |
| 4,716,119 | 12/1987 | Rehner et al. | 436/16 |
| 4,839,279 | 6/1989 | Kosaka et al. | 435/25 |
| 5,028,542 | 7/1991 | Kennamer et al. | 436/14 |
| 5,147,777 | 9/1992 | Sutton et al. | 435/5 |
| 5,177,023 | 1/1993 | Sutton et al. | 436/533 |
| 5,240,735 | 8/1993 | Lau | 422/56 |
| 5,260,195 | 11/1993 | Azhar et al. | 435/25 |

Primary Examiner—James C. Housel
Assistant Examiner—N. Bhat
Attorney, Agent, or Firm—Felfe & Lynch

[57] ABSTRACT

Described are control reagents useful in analyte determination. The reagents contain a known concentration or amount of the analyte to be assayed, and a polymer. The polymer is made up of monomers of either water soluble acrylic monomers, water soluble quaternary amines, or mixtures of these two types of molecules. Various control reagent formulations, as well as new polymers useful in control reagents, are disclosed.

16 Claims, No Drawings

POLYMER CONTAINING CONTROL REAGENTS AND POLYMERS USEFUL IN CONTROL REAGENTS

FIELD OF THE INVENTION

Described are control reagents useful in validating testing devices, such as test strips and dipsticks. More particularly, it relates to a non-serum based, aqueous control reagent.

BACKGROUND AND PRIOR ART

The field of clinical chemistry and clinical analysis is concerned, inter alia, with the determination and quantification of various substances in body fluids. Many examples of substances which are to be determined can be given, and include cholesterol, urea, cations, and glucose. These examples of analyte as well as others, are assayed in diverse body fluids such as urine and blood.

One of the most frequently used devices in clinical chemistry is the test strip or dipstick. These devices are characterized by their simplicity of use. Essentially, the device is contacted to the body fluid to be tested. Various reagents incorporated into the device react with the analyte being determined to provide a detectable signal. Generally, this is a color or a change in color. These signals are measured or determined either visually or, more preferably, by an analysis machine. The detectable signal is correlated to a standard, so as to give a value for the amount of analyte present in the sample.

It will be understood that clinical analysis of the type described herein requires that any testing system be extremely accurate. In particular, when automated systems are used, it is essential to ensure that the elements of the analysis be reliable, and that the measurement taken be valid. It is for this purpose that control reagents are used.

Tietz et al., Textbook of Clinical Chemistry page 430, defines "control material" as "a specimen, or solution, which is analyzed solely for quality control purposes and is not used for calibration purposes". This standard reference work goes on to describe some of the requisite of a control material, as follows: "They need to be stable materials, available in aliquots or vials, that can be analyzed periodically over a long time. There should be little vial-to-vial variation so that differences between repeated measurements can be attributed to the analytical method alone". It must be added that the control material must be stable as well.

The cited reference, at page 433, discusses how the matrix of the control material should be the same as the material being analyzed. To that end, Tietz discusses modified human serum as one type of control material. Indeed, the art now recognizes the term "control serum" as referring to control material based upon serum. This terminology will be used herein, and is different from the term "control reagent" which, as used hereafter, refers to a control material which is not based on, and does not control serum of any type.

As has been pointed out, supra, one of the criteria which control materials have to satisfy is stability. Control materials based upon serum, however, are inherently unstable, due to the various components contained therein. Further, sera will vary from source to source, so uniformity from lot to lot cannot be guaranteed. Thus, it is sometimes desirable to have a control material based on a non-serum or serum free medium.

Examples of serum free control media, or "control reagents" as used herein, are seen in U.S. Pat. Nos. 4,684,615 and 4,729,959. The '615 patent teaches an aqueous isoenzyme control reagent. The reagent contains the isoenzyme of interest, together with other materials in a water base. More pertinent to the subject invention is the '959 patent, which is directed to "a stable glucose reference control". This control contains glucose in a range of from abut 40 to 500 mg/dl, together with fixed red blood cells, in an aqueous solution. The range of glucose concentrations given are sufficient to cover just about all ranges of glucose found in, e.g., blood.

The '959 patent points to a problem with aqueous control reagents at column 1, lines 50–55. Briefly, erythrocytes impart a degree of viscosity to blood which is absent in water based systems. This problem was also recognized in U.S. Pat. No. 3,920,580 to Mast. This patent teaches that aqueous solutions had not been consistent, and that a lack of reproduceability was observed when dry reagent strips were used with such materials. Mast taught that suitable reagents could be prepared using an antidiffusing agent in combination with glucose and water. The antidiffusing agents include polyvinylpyrrolidone, polyvinyl alcohol, polyethylene glycol, dextran, and bovine serum albumin. In U.S. Pat. No. 5,028,542, an invention is described wherein polystyrene sulfonates are added to aqueous glucose solutions. The polystyrene compounds are added so as to render the viscosity of the control reagents more similar to whole blood or serum.

An additional drawback to water based control reagents is exaggerated color formulation. The reaction which is monitored for analyte determination is generally one involving color formulation. Whole blood, of course, has a distinct red color, and serum is tinted differently than plan water. As a result, even when identical concentrations of the analyte of interest are present, and the same reaction system is used, a different degree of color formation results. While this problem can be addressed, in part, by use of suitable "control constants" or "control curves", it would be desirable to have control reagents available where the problem is eliminated or reduced.

The approach taken in the invention disclosed herein is somewhat similar to that of U.S. Pat. No. 5,028,542 in that polymers are used to address the problem of viscosity adjustment; however, the '542 patent does not disclose that polymers can be used to compensate for exaggerated color formation. Additionally, it is surprising that the polymers described herein possess the properties they do in control reagents, as they are not related to the polystyrenes of the '542 patent.

In a preferred embodiment of the invention, the polymers themselves are new. The polymers are based upon water soluble acrylic monomers, water soluble quaternary amines, or combinations thereof. The polymers are combined, in an aqueous solution, together with a predefined amount of a particular analyte of interest. The resulting material is useful as a serum free control reagent for use in determining unknown amounts of the particular analyte.

How the invention and its goals are achieved is set forth in the disclosure which follows.

DETAILED DESCRIPTION OF PREFERRED EMBODIMENTS

A. Preparation of Polymers

The following examples describe the preparation of new polymers which are useful in the practice of the invention. In each case, the polymer is prepared by combining an amount of a monomer and a catalyst (e.g., ammonium persulfate) in a solvent (e.g., water). Following admixing, the solutions were purged with $N_2$ gas, and then incubated at 75° C. in a water bath for anywhere from 4 to 6 hours. There was no need to isolate the resulting polymers from the solutions following the reactions—i.e., they were combined into serum free control reagents directly.

EXAMPLE 1

| | |
|---|---|
| Monomer: 2-aminoethylmethacrylate.HCl | 33.00 g |
| Catalyst: ammonium persulfate | .33 g |
| $H_2O$: | 66.67 g |
| Total: | 100 g |

EXAMPLE 2

| | |
|---|---|
| Monomer: N-(3-aminopropyl) methacrylate | 33.00 g |
| Catalyst: ammonium persulfate | .33 g |
| $H_2O$: | 66.67 g |
| Total: | 100 g |

EXAMPLE 3

| | |
|---|---|
| Monomer: Dimethylaminoethylmethacrylate DMSO | 50.00 g |
| Catalyst: ammonium persulfate | .40 g |
| $H_2O$: | 71.1 g |
| Total: | 121.5 g |

EXAMPLE 4

| | |
|---|---|
| Monomer: Dimethylaminoethylmethacrylate HCl | 50.00 g |
| Catalyst: ammonium persulfate | .375 g |
| $H_2O$: | 60.75 g |
| Total: | 111.125 g |

The above identified monomers all yield cationic polymers.

EXAMPLE 5

| | |
|---|---|
| Monomer: Glacial Acrylate | 30.0 g |
| Catalyst: ammonium persulfate | .3 g |
| $H_2O$: | 70.0 g |
| Total: | 100.3 g |

EXAMPLE 5 represents preparation of an anionic polymer.

EXAMPLE 6

| | |
|---|---|
| Monomer 1: Glacial acrylate | 12.5 g |
| Monomer 2: Dimethylaminoethylmethacrylate HCl | 16.66 g |
| Catalyst: ammonium persulfate | .25 g |
| $H_2O$: | 71.85 g |
| Total: | 101.26 g |

EXAMPLE 7

| | |
|---|---|
| Monomer: Trimethylammoniumethyl methacrylic chloride | 6.25 g |
| Catalyst: ammonium persulfate | 0.1 g |
| $H_2O$: | 43.75 g |
| Total: | 50.1 g |

Examples 6 and 7 represent preparation of amphoteric polymers.

EXAMPLE 8

The 2-aminoethylmethacrylate polymer ("N-1" hereafter), prepared in accordance with Example 1, was tested as a component of a glucose control. In this experiment, a 0.4% solution of the polymer (pH 7.4; viscosity 235), was added to about 200 ml of $H_2O$, after which the solution was then added to 250 ml of $H_2O$. This solution was then used in combination with glucose or glucose plus a buffer of MES/CAPS. Glucose was added from spiked solutions of 2000 ml/dl or 20,000 mg/dl, diluted to yield concentrations over a range of 10 to 800 mg/dl, with the exception of the N-1 polymer, which was tested up to 600 mg/dl. Samples (4 ml) were taken, and added to polymer dispersions as described supra, in 5 ml culture tubes. The resulting materials were tested in a reflectometer yielding the curve set forth in FIG. 1. The first measurement was taken 10 seconds after placing in the instruments, and the total residence time was 20 seconds. The curve indicates the usefulness of the polymer as a control.

EXAMPLE 9

Glucose + ATP $\xrightarrow{\text{hexokinase}}$ Glucose-6-phosphate + ADP

Glucose-6-phosphate + NADP (NAD+) $\xrightarrow{\text{G-6-PD}}$ 6-phosphogluconate + NADPH (NADH) + H+

A well known method of determining glucose concentration in a sample is the "HK" or "hexokinase" system, i.e.:
When NADPH (NADH) is present, absorbance caused by the compound is measured as a direct determination of glucose in the sample.

The HK system was used in tests on two different measuring systems, i.e., the "Hitachi 705" and the "YSI Glucose system". Polymers "PAQ-MC1", "C-1", "N-1" and "N-2", corresponding to polymers of dimethylaminoethylmethacrylate-methylchloride ("PAQ-MC1"); dimethylaminoethyl methacrylate and glacial acetic acid ("C-1"), the polymer of Example 1, and N-3-aminopropylmethacrylate ("N-2") were tested. The polymers were tested against concentrations of glucose at 0, 50, 200 and 500 mg/dl. The values obtained were as follows:

TABLE 1

| | 0 mg/dl | 50 mg/dl | 200 mg/dl | 500 mg/dl |
|---|---|---|---|---|
| | | Hitachi 705 | | |
| PAQ-MC1 | 43 | 101 | 246 | 529 |

TABLE 1-continued

|  | 0 mg/dl | 50 mg/dl | 200 mg/dl | 500 mg/dl |
|---|---|---|---|---|
| C-1 | 0 | 56 | 202 | 491 |
| N-1 | 6 | 66 | 215 | 506 |
| N-2 | 33 | 92 | 237 | 535 |
| YSI Glucose | | | | |
| PAQ-MCl | 2 | 52 | 181 | 436 |
| C-1 | 0 | 58 | 209 | 508 |
| N-1 | 0 | 57 | 164 | 407 |
| N-2 | 1 | 55 | 187 | 455 |

The values suggest that in the hexokinase system, amphoteric amine polymers are better. Cationic materials appear to interact with the NAD+/NADH in the system.

EXAMPLE 10

A series of experiments were carried out on the polymers referred to as "N-1" and "C-1", supra. The experiments tested the effect of different buffers and pHs on the polymers used as glucose controls. In these experiments, solutions were prepared containing the polymer and buffers at various concentrations and pH's. Glucose was added to the solutions, and 17 ul of each final solution was tested, and reflectance values were determined, using a reflectometer. These results follow. In the tables, the value in parenthesis represents the "target value" of the solution being tested. To elaborate, each solution was "spiked" to attain a specific glucose concentration. The particular concentration sought is in parenthesis. The first value is the actual amount of analyte in the tested sample.

TABLE 2

| Buffer | Polymer N-1 | | |
|---|---|---|---|
|  | pH | HK value (mg/dl) | % Reflectance |
| Phosphate, 25 mM | 6.0 | 127(150) | 38.58 |
| Phosphate 25 mM | 6.0 | 127.5 (60) | 38.1 |
| HEPES 150 mM | 8.0 | 58 (60) | 47.54 |
| HEPES 150 mM | 8.0 | 58.5 (60) | 48.99 |
| TRIS 150 mM | 6.0 | 140 (150) | 33.88 |
| HEPES 25 mM | 8.0 | 160 (150) | 43.03 |
| TRIS 25 mM | 6.0 | 40 (60) | 46.83 |
| TRIS 150 mM | 8.0 | 94 (150) | 45.09 |
| TRIS 150 mM | 6.0 | 141 (150) | 32.17 |
| Phosphate 25 mM | 6.0 | 58 (60) | 43.43 |
| HEPES 150 mM | 6.0 | 43 (60) | 52.83 |
| TRIS 25 mM | 8.0 | 143 (150) | 38.59 |

TABLE 3

| Buffer | Polymer C-1 | | |
|---|---|---|---|
|  | pH | HK value | % Reflectance |
| TRIS 150 mM | 6.0 | 51.5 (60) | 52.34 |
| Phosphate 150 mM | 8.0 | 57 (60) | 51.59 |
| HEPES 25 mM | 6.0 | 134 (150) | 40.77 |
| Phosphate 150 mM | 8.0 | 58 (60) | 45.82 |
| TRIS 150 mM | 8.0 | 56 (60) | 51.59 |
| TRIS 150 mM | 6.0 | 53 (60) | 46.03 |
| Phosphate 150 mM | 8.0 | 57 (60) | 43.64 |
| TRIS 25 mM | 8.0 | 58 (60) | 53.64 |
| TRIS 25 mM | 6.0 | 137 (150) | 37.14 |
| TRIS 25 mM | 6.0 | 136 (60) | 33.48 |
| TRIS 25 mM | 8.0 | 57 (60) | 51.76 |
| HEPES 25 mM | 6.0 | 54 (60) | 44.56 |
| HEPES 25 mM | 6.0 | 59 (60) | 45.53 |
| Phosphate 150 mM | 6.0 | 55 (150) | 49.81 |
| HEPES 150 mM | 6.0 | 140 (150) | 43.84 |
| HEPES 25 mM | 6.0 | 59 (60) | 49.67 |

The foregoing indicates that the polymers of the invention are useful in preparing control reagents. The data show that an appropriate dose response is generated—i.e., more color forms (the "HK" values), and the percent reflectance decreases (the "%R" values), as the concentration of analytes increases. While the actual "signal" generated will vary based on parameters such as the buffer and the pH employed, these variations do not alter the usefulness of the controls for testing analytes, such as glucose. Other analytes, and other buffers besides those expressly described herein may be used, as the artisan of ordinary skill will readily ascertain.

The preceding examples describe the synthesis of various polymers and their use in control reagents. The control reagents comprise a known concentration of an analyte to be determined, and a polymer of the type described herein. Specifically, the polymers are (i) water soluble acrylic monomer based polymers, and (ii) water soluble quaternary amine based polymers. The choice of which category of polymers to use will depend on a number of factors within the control of the artisan including, e.g., the nature of the detection reactions used to determine the analyte of interest.

The control reagents may be used in any of a number of forms. For example, the control reagent may be presented as a solution or lyophilisate. In the latter case, lyophilized control reagent may be impregnated or otherwise incorporated into a diagnostic test strip, membrane, film, or some other type of analytical apparatus. It is also possible to present the control reagent as a kit, where the components are presented in a mixed type of system. For example, the polymer may be present in solution form with the analyte of interest in dried form, and vice versa. In such kits, of course, the components are presented in separate portions.

The control reagents may also contain a buffer, such as HEPES, TRIS, phosphate buffer, or other buffers such as those described in U.S. Pat. No. 5,028,542 to Kennamer et al., the disclosure of which is incorporated by reference. Other materials which may be included in the control reagent include preservatives, surfactants, biocides, and so forth, such as those described in the above-identified patent, these also being incorporated by reference herein. Other ingredients which may be included are coloring agents, viscosity modifiers, and so forth.

The analyte in known concentration is preferably glucose, but may also be any of the well known analytes assayed for in the body fluids, including cholesterol, uric acid, various ketones, creatine or creatinine, and so forth. Of particular interest in the invention are the polymers listed in Examples 1–7 of the foregoing disclosure, including polymers of 2-aminoethylmethacrylate. HCl; N-3-aminopropylmethacrylate; dimethylaminoethylmethacrylate DMSO; dimethylaminoethylmethacrylate.HCl; and glacial acrylate. The foregoing are all examples of cationic polymers. Additionally, anionic polymers, such as polymers of glacial acrylate and glacial methacrylate, and amphoteric polymers, such as polymers of glacial acrylate/dimethyl-aminoethylmethacrylate.HCl, and trimethylammoniumethyl methacrylic chloride are embraced by this invention. Particularly preferred are polymers of 2-aminoethylmethacrylate and glacial acrylate/dimethyl-aminoethylmethacrylate.

The polymers described herein are new. They are prepared by combining their constituent monomers with a catalyst, and then treating the resulting mixture so as to lead to polymerization of the molecules. Preferred parameters, including catalyst ammonium persulfate and reaction conditions are set forth supra, and need not be repeated here.

The terms "quaternary ammonium", "acrylic monomer" and "glacial" as used in the foregoing disclosure are used in accordance with the definitions traditionally given for each, as represented by, e.g., *Grant & Hackh's Chemical Dictionary*, or any of the standard reference works known to the artisan of ordinary skill. All terms employed herein are to be interpreted in accordance with standard usage in the art.

The foregoing examples are given for purposes of illustrating the invention, and are not to be construed as limitations on the scope thereof.

It will be understood that the specification and examples are illustrative but not limitative of the present invention and that other embodiments within the spirit and scope of the invention will suggest themselves to those skilled in the art.

We claim:

1. Control reagent solution, comprising:
   (i) a known concentration of an analyte to be determined, and
   (ii) at least one member selected from the group consisting of (a) a water soluble acrylic monomer based polymer, and (b) a water soluble quaternary amine based polymer, wherein (i) and (ii) are present together in said solution.

2. The control reagent of claim 1, wherein said polymer is a polymer of 2-aminoethylmethacrylate.

3. The control reagent of claim 1, wherein said polymer is a polymer of N-(3-aminopropyl methacrylate).

4. The control reagent of claim 1, wherein said polymer is a polymer of dimethylaminoethyl methacrylate-DMSO.

5. The control reagent of claim 1, wherein said polymer is a polymer of dimethylaminoethyl methacrylate.HCl.

6. The control reagent of claim 1, wherein said analyte is glucose.

7. The control reagent of claim 1, wherein said analyte is cholesterol.

8. The control reagent of claim 1, further comprising a coloring agent.

9. Method for determining an analyte in blood sample, comprising the steps of:
   (a) admixing said blood system with a first portion of a reaction system which determines said analyte,
   (b) admixing the control reagent solution of claim 1 with a second portion of said reaction system, and
   (c) comparing any reaction observed in step (a) to any reaction observed in step (b) as a determination of analyte in said blood sample.

10. The method of claim 9, wherein said analyte is glucose.

11. The method of claim 9, wherein said analyte is cholesterol.

12. A lyophilized control reagent, comprising:
    (i) a known concentration of an analyte to be determined, and
    (ii) at least one member selected from the group consisting of (a) a water soluble acrylic monomer based polymer, and (b) a water soluble quaternary amine based polymer, wherein (i) and (ii) are present together in said lyophilized control reagent.

13. Control reagent solution consisting essentially of:
    (i) a known concentration of an analyte to be determined, and
    (ii) at least one member selected from the group consisting of (a) a water soluble acrylic monomer based polymer, and (b) a water soluble quaternary amine based polymer, wherein (i) and (ii) are present together in said solution.

14. Analytical test apparatus comprising a solid phase having the control reagent of claim 13 impregnated thereon.

15. The analytical test apparatus of claim 14, wherein said solid phase is a bibulous paper strip.

16. Lyophilized control reagent consisting essentially of:
    (i) a known concentration of an analyte to be determined, and
    (ii) at least one member selected from the group consisting of (a) a water soluble acrylic monomer based polymer, and (b) a water soluble quaternary amine based polymer wherein (i) and (ii) are present together in said lyophilized control reagent.

* * * * *